US00PP26385P3

(12) United States Plant Patent
Oates

(10) Patent No.: US PP26,385 P3
(45) Date of Patent: Feb. 2, 2016

(54) ***ECHEVERIA* PLANT NAMED 'ECRAQ03-0'**

(50) Latin Name: *Echeveria gibbiflora*
Varietal Denomination: ECRAQ03-0

(71) Applicant: John David Oates, Tura Beach (AU)

(72) Inventor: John David Oates, Tura Beach (AU)

( * ) Notice: Subject to any disclaimer, the term of this patent is extended or adjusted under 35 U.S.C. 154(b) by 314 days.

(21) Appl. No.: 13/987,155

(22) Filed: Jul. 3, 2013

(65) Prior Publication Data

US 2015/0020254 P1 Jan. 15, 2015

(51) Int. Cl.
*A01H 5/02* (2006.01)

(52) U.S. Cl.
USPC ..... Plt./373
CPC ..... *A01H 5/02* (2013.01)

(58) Field of Classification Search
USPC ..... Plt./373, 263.1
CPC ..... A01H 5/02; A01H 5/00
See application file for complete search history.

*Primary Examiner* — Kent L Bell
(74) *Attorney, Agent, or Firm* — Cassandra Bright

(57) ABSTRACT

A new and distinct *Echeveria* cultivar named 'ECRAQ03-0' is disclosed, characterized by a non-branching rosulate plant form, long pink scape, unique leaf margin coloration and tight leaf edge undulations. Additionally, leaf color varies with temperature. The new variety is an *Echeveria*, normally produced as an ornamental garden or container plant.

2 Drawing Sheets

Figure 1:
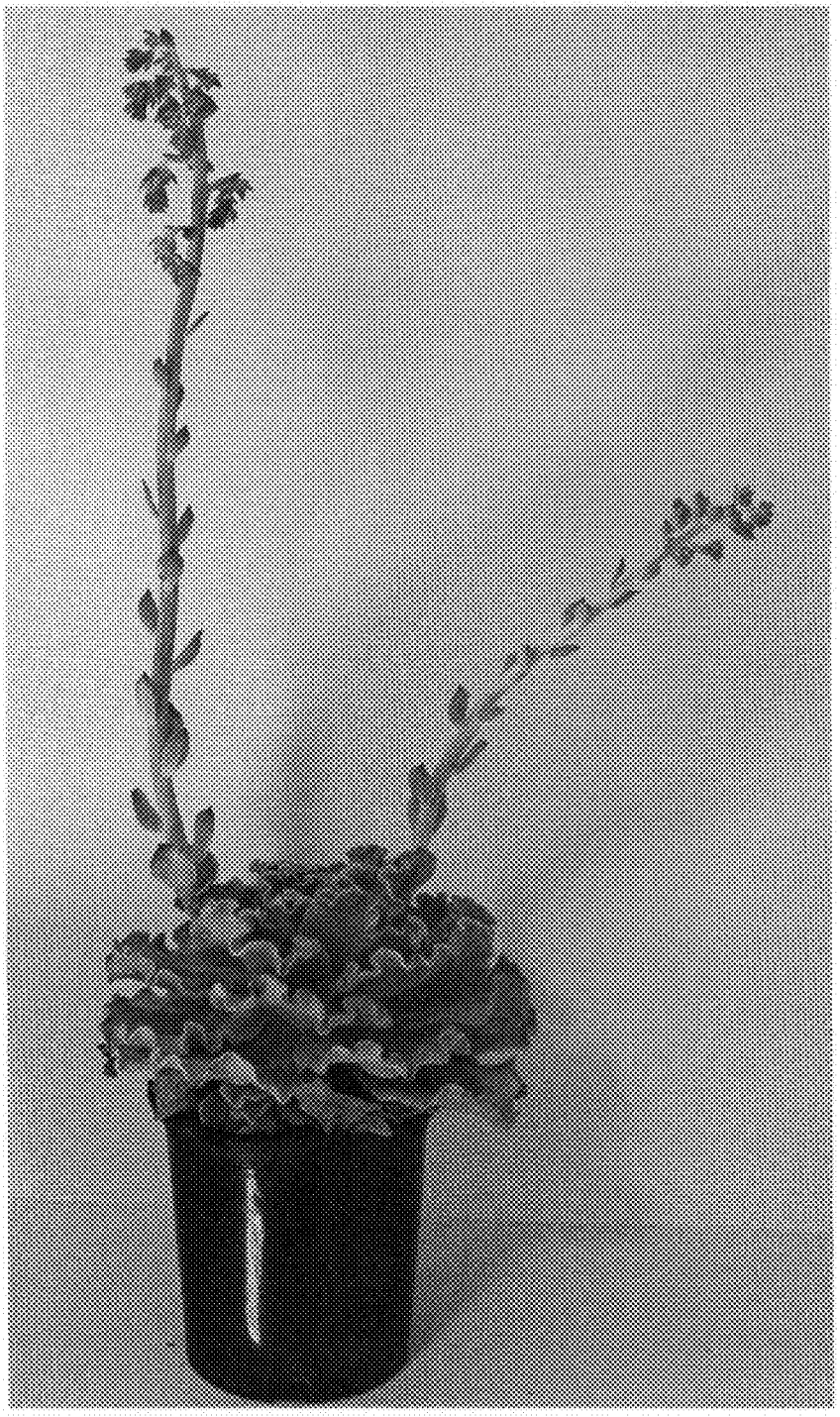

Latin name of the genus and species: *Echeveria gibbiflora*.
Variety denomination: 'ECRAQ03-0'.

BACKGROUND OF THE INVENTION

The new *Echeveria* cultivar is a product of a planned breeding program conducted by the inventor, John Oates, in Macquaires Fields, Australia. The objective of the breeding program was to produce new *Echeveria* varieties for ornamental commercial applications. The new variety is a product of crossbreeding that occurred on May 4, 2004, at a commercial nursery in Macquaires Fields, Australia. The new variety was selected during July of 2006 from seedlings resulting from this 2004 crossing.

The seed parent is the unpatented, proprietary seedling variety *Echeveria gibbiflora*, 'Line 127'. The pollen parent is the unpatented, proprietary seedling variety *Echeveria gibbiflora*, 'Line 176'. The new variety was discovered during July of 2006 by the inventor in a group of seedlings resulting from the 2004 crossing, in a commercial nursery in Macquaires Fields, Australia.

Asexual reproduction of the new cultivar has been performed by tissue culture. This was first performed at a laboratory in Tumbi Umbi, Australia in January of 2008 and has shown that the unique features of this cultivar are stable and reproduced true to type in 15 successive generations.

SUMMARY OF THE INVENTION

The cultivar 'ECRAQ03-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ECRAQ03-0'. These characteristics in combination distinguish 'ECRAQ03-0' as a new and distinct *Echeveria* cultivar:

1. Leaf margin has distinctive red coloration at all temperatures.
2. Leaf blade color varies with temperatures; Winter dark red, Summer medium green.
3. Rosulate plant form, non branching.
4. Leaf edge with a strong, tight undulation.
5. Long scape of a medium pink color.

PARENT COMPARISON

Plants of the new cultivar 'ECRAQ03-0' are similar to plants of the seed parent, unpatented, proprietary seedling variety of *Echeveria gibbiflora* 'Line 127' in most horticultural characteristics, however, plants of the new cultivar 'ECRAQ03-0' produce a leaf margin with finer and more consistent undulation than the seed parent. Additionally, 'ECRAQ03-0' produces leaves of different coloration than those of the seed parent.

Plants of the new cultivar 'ECRAQ03-0' are similar to plants of the pollen parent; *Echeveria gibbiflora* 'Line 176' in most horticultural characteristics, however, plants of the new cultivar 'ECRAQ03-0' produce with a consistent undulation along the margin than the pollen parent. Additionally, the pollen parent exhibits different foliage coloration than the new variety.

COMMERCIAL COMPARISON

'ECRAQ03-0' can be compared to the commercial variety *Echeveria gibbiflora* 'ECRPI01-0', U.S. Plant Pat. No. 25,269. Plants of 'ECRAQ03-0' are similar to plants of 'ECRPI01-0' in most horticultural characteristics, however, plants of 'ECRAQ03-0' produce leaves with a tightly undulated edge that is red in all temperatures, which is not the case with the comparator. Additionally, 'ECRAQ03-0' produces leaves that changes color as temperatures changes: dark red in winter, medium green in summer. The comparator does not change color with temperature change.

'ECRAQ03-0' can be compared to the commercial variety *Echeveria gibbiflora* 'ECRRE02-0', U.S. Plant Pat. No. 25,282. Plants of 'ECRAQ03-0' are similar to plants of 'ECRRE02-0' in most horticultural characteristics, however, plants of 'ECRAQ03-0' produce leaves with a tightly undulated edge that is red in all temperatures, which is not the case with the comparator. Additionally, 'ECRAQ03-0' produces foliage that changes color as temperatures changes: dark red in winter, medium green in summer. The comparator does not change color with temperature change.

BRIEF DESCRIPTION OF THE PHOTOGRAPHS

The accompanying photograph in FIG. 1 illustrates in full color a close up of typical foliage of 'ECRAQ03-0'.

Figure 2:
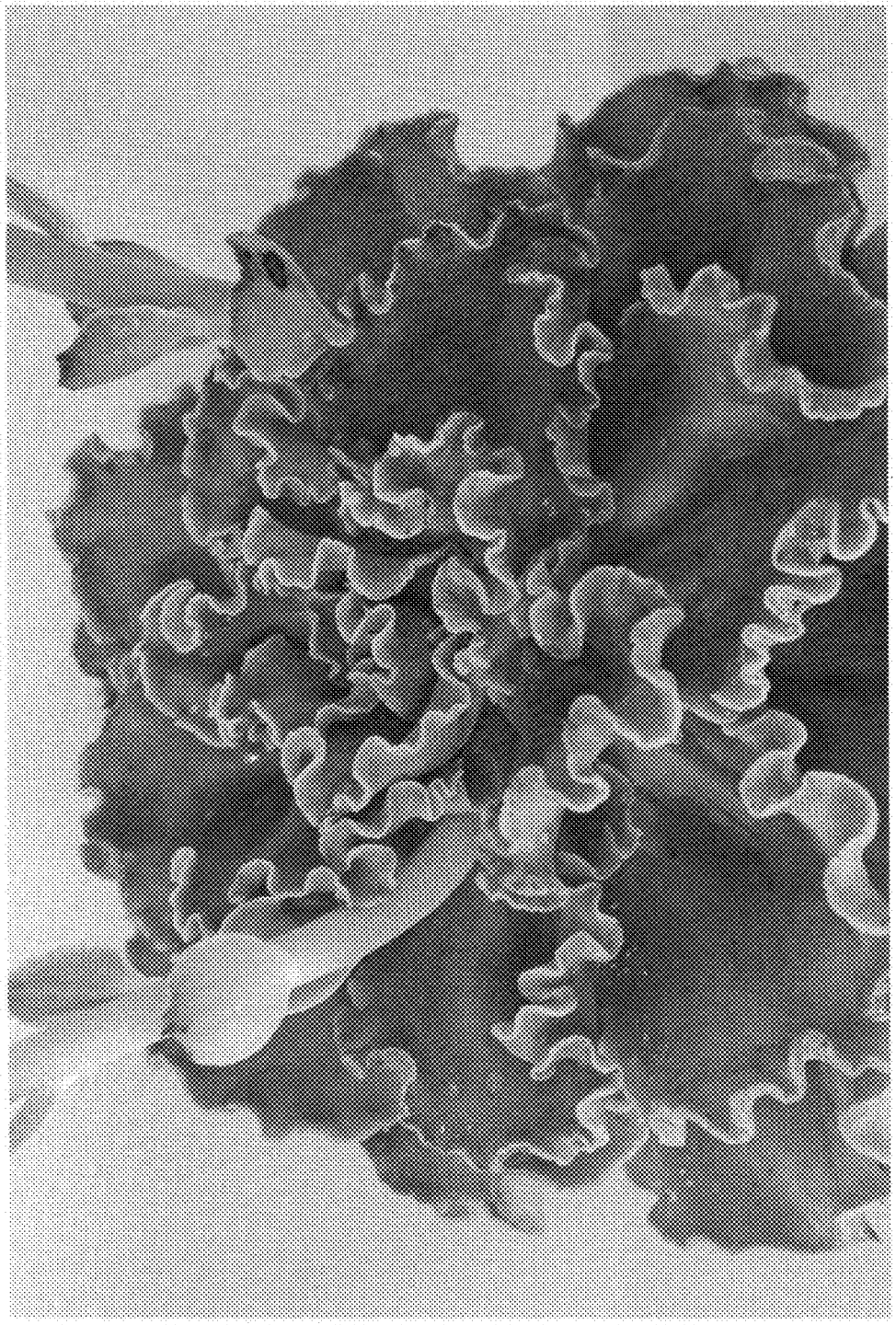

FIG. 2 illustrates a flowering plant.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'ECRAQ03-0' plants grown in a greenhouse in Oxnard, Calif. The growing temperature ranged from approximately 15° C. to 28° C. during the day and from 12° C. to 22° C. during the night. General light conditions are bright, normal sunlight. Measurements and numerical values represent averages of typical plant types. Measurements were taken from plants grown in warm temperatures, during Spring and Summer.

Botanical classification: *Echeveria gibbiflora* 'ECRAQ03-0'.

PROPAGATION

Propagation method: Tissue culture.

PLANT

Age of plant described: Approximately 14 months from tissue culture.

Container size: 1 gallon nursery container.

Growth habit.—Central Rosette.

Height: Approximately 14 cm to top of highest leaf. Approximately 60 cm to top of inflorescence.

Plant spread: Approximately 26 cm.

Growth rate: Slow.

Branching characteristics: Non branching, single rosette formation. To date, only a single rosette, without branches has been observed.

FOLIAGE

Leaf:

*Arrangement*.—Rosette.

*Average length*.—Approximately 10 cm.

*Average width*.—Approximately 11 cm.

*Shape of blade*.—Spatulate.

*Apex*.—Rounded crenulate.

*Base*.—Obuse.

*Margin*.—Undulating and crenulate.

*Texture of top surface*.—Glabrous.

*Texture of bottom surface*.—Glabrous.

*Quantity of leaves per plant*.—Approximately 18 large leaves, and 10 smaller immature inner leaves.

*Color*.—Young foliage upper side: Near RHS Green 138D; margin near RHS Yellow-Green 145D; irregular margin spots near RHS Red-Purple 61B. Young foliage under side: Near RHS Green 138D; margin near RHS Yellow-Green 145D; irregular margin spots near RHS Red-Purple 61B. Mature foliage upper side: Near RHS Green 138B; margin near RHS Yellow-Green 145C: irregular flushing near RHS Red 53C; irregular spots near RHS Red 53B. Mature foliage under side: Near RHS Green 138B: margin near RHS Yellow-Green 145C; irregular flushing near RHS Red 53C: irregular spots near RHS Red 53B.

*Cold temperature color*.—Young foliage upper side: Near RHS Green 138D; margin near RHS Greyed-Purple 185B. Heavy flushing from margin, down towards leaf blade near Greyed-Red 181B. Young foliage under side: Near RHS Green 138D; margin near RHS Red 53B, irregular margin spots near RHS Greyed-Purple 185B. Moderate flushing from margin, down towards leaf blade near Greyed-Red 181B. Mature foliage upper side: Near RHS Green 138B; very end of margin near RHS Red 53B. Heavy flushing from margin near Greyed-Purple 185A. Mature foliage under side: Near RHS Green 138B: very end of margin near RHS Red 53B. Moderate flushing from margin near Greyed-Purple 185A.

Venation:

*Type*.—Linear.

*Venation color upper side*.—Indistinguishable from foliage.

*Venation color under side*.—Indistinguishable from foliage.

FLOWER

Inflorescence type and habit: Heterothetic compound raceme.

Rate of flower opening: More than 2 weeks to a fully opened flower.

Flower longevity on plant: Several weeks.

Quantity of flowers: Approximately 30 maturing buds and flowers per inflorescence.

Total inflorescence size, including floral stem:

*Height*.—Approximately 58 cm.

*Width*.—Approximately 17 cm.

*Individual racemes per inflorescence*.—Average 9.

Individual raceme size, including peduncle:

*Height*.—Approximately 6 cm.

*Width*.—Approximately 8 cm.

*Individual flowers per raceme*.—Average 4 or 5.

Individual flowers:

*Arrangement*.—Cylindrical shaped corolla, actinomorphic. 5 separate petals, nearly fully fused from base.

*Size*.—Length: Approximately 1.4 cm. Width: Approximately 1.4 cm at widest point. Unfused petal length: Approximately 0.4 cm. Unfused petal width: Approximately 0.5 cm.

*Margin*.—Entire.

*Apex*.—Acute, somewhat sharp.

*Base*.—Fused.

*Texture*.—Glabrous, fleshy and hard.

*Shape*.—Deltate.

Color:

*Petals*.—When opening: Outer surface: Base color near RHS Red 38A, mid section near RHS Red 44D, Apex and Margins near RHS Red 44B. Inner surface: Base color near RHS Red 36D, mid section near RHS Orange 29C, Apex near RHS Red 42A. Fully opened: Outer surface: Near RHS Red 38D at base, mid section near RHS Red 43C, margins near Red 45B, apex near RHS Red 46A. Inner surface: Base color near Red 36D, mid section near RHS Orange 29C, Apex near RHS Red 42A. Color Changes when Ageing: Petals close tightly together with age, interior no longer visible. Exterior color: base near RHS Greyed-Purple 186D, changing to near RHS Greyed-Purple 187B in upper 70%.

Bud:

*Shape*.—Oblong.
*Length*.—Approximately 1.2 cm.
*Diameter*.—Approximately 1.1 cm.
*Color*.—Base near RHS Red 36 D, mid section heavily flushed with near RHS Orange-Red 35A, tip near RHS Red 46A.

Sepals:

*Length*.—Approximately 0.7 cm.
*Width*.—Approximately 0.4 cm.
*Shape*.—Deltoid.
*Apex*.—Acute.
*Base*.—Blunt.
*Margin*.—Entire.
*Texture*.—Glabrous, fleshy.
*Color*.—Upper and lower surfaces Near RHS Yellow-Green 146B, Margin and apex flushed near RHS Red 46A.

Pedicels:

*Length*.—Approximately 0.5 cm.
*Width*.—Approximately 0.2 cm.
*Aspect*.—Approximately 45° angle, or less to peduncle, straight.
*Color*.—Near RHS Greyed-Green 194C, with completely overlay color of near RHS Orange-Red 35C.
*Strength*.—Very strong.
*Texture*.—Glabrous, fleshy.

Peduncles:

*Length*.—Average 4.5 cm.
*Width*.—Approximately 0.4 cm.
*Aspect*.—Approximately 45° angle, to scape, straight.
*Color*.—Near RHS Greyed-Green 193B, flushed with near RHS Red 46D.
*Strength*.—Very strong.
*Texture*.—Glabrous, fleshy.

Scape:

*Length*.—Approximately 38 cm to bottom of first peduncle.
*Width*.—Approximately 1.4 cm.
*Angle*.—Arising at a 90° angle from foliar rosette.
*Strength*.—Very strong.
*Color*.—Near RHS Greyed-Green 193C, flushed with near RHS Red 46C. Red flushing much more prominent with maturity of scape and flowers.

Scape scales:

*Length*.—Average 3.5 cm.
*Width*.—Approximately 2.0 cm.
*Aspect*.—Approximately 45° angle, or less, to scape, straight.
*Color*.—Near RHS Yellow-Green 144C, margin and apex flushed near RHS Red 46D.
*Texture*.—Glabrous, fleshy.

Fragrance: None.

REPRODUCTIVE ORGANS

Stamens:

*Number*.—Average 10.
*Filament length*.—Approximately 0.5 cm.
*Filament color*.—Near RHS White N155D.
*Anther length*.—Approximately 0.1 cm.
*Anther color*.—Near RHS Greyed-Orange 166A.
*Anther shape*.—Oblong.
*Pollen*.—Near RHS White 155A.
*Pollen quantity*.—Scant.

Pistil:

*Number*.—5.
*Length*.—Approximately 1 cm.
*Style color*.—Near RHS Greyed-Purple 187A.
*Stigma*.—Shape: Linear. Color: Near RHS Greyed-Purple 187A. Ovary color: Near RHS Greyed-Green 193C. Ovary Shape: Ovoid. Ovary Diameter: Approximately 0.4 cm. Ovary Length: Approximately 0.5 cm.

OTHER CHARACTERISTICS

Seeds and fruits: No seeds-fruits detected to date.

Disease/pest resistance: Neither resistance nor susceptibility to the normal diseases and pests of *Echeveria* have been observed.

Temperature tolerance: Tolerates temperatures from approximately 0° C. to at least 40° C.

What is claimed is:

1. A new and distinct cultivar of *Echeveria* plant named 'ECRAQ03-0' as herein illustrated and described.

* * * * *